United States Patent [19]

Naono

[11] 4,120,661

[45] Oct. 17, 1978

[54] SAMPLING DEVICE

[75] Inventor: Toyohiko Naono, Tokyo, Japan

[73] Assignee: Nihon Denshi Kabishiki Kaisha, Tokyo, Japan

[21] Appl. No.: 882,450

[22] Filed: Mar. 1, 1978

[30] Foreign Application Priority Data

Mar. 3, 1977 [JP] Japan .................. 52-22990

[51] Int. Cl.² ................................. G01N 1/14
[52] U.S. Cl. ................................. 422/68; 73/425.6
[58] Field of Search ............ 23/259, 253 R, 230 R; 73/425.6, 425.4 R

[56] References Cited

U.S. PATENT DOCUMENTS

| | | | |
|---|---|---|---|
| 3,222,135 | 12/1965 | Ashmead | 23/259 X |
| 3,476,518 | 11/1969 | Jungner | 23/259 |
| 3,484,207 | 12/1969 | Anthon | 23/259 X |
| 3,525,592 | 8/1970 | Buckley | 23/259 |
| 3,567,390 | 3/1971 | Rothermel | 23/259 |
| 3,948,607 | 4/1976 | Atwood et al. | 23/259 |

Primary Examiner—R.E. Serwin

Attorney, Agent, or Firm—Webb, Burden, Robinson & Webb

[57] ABSTRACT

A rotating valve body and a fixed valve body, said rotating body and fixed body having radial surfaces in sliding contact. The radial surface of the rotating body is provided with one or more internal sampling outlet ports arranged on the circumference of a circle having a center coincident with the axis of the rotating body. The side wall of said rotating body is provided with one or more external sampling inlet ports. Pairs of unlike ports are connected by ducts in said rotating body. The external sample inlet ports are connected to a sample tube, or tubes or sample suction tube or tubes which rotate together with the rotating valve body. The radial surface of the fixed valve body is provided with a single internal sample inlet port located the same distance from the axis as the internal sample outlet ports. The internal sample inlet port is directly linked to two ports in the sidewall of the fixed valve body by two ducts which join together at the internal inlet, said ducts being connected to a reagent tank via a sampling pump, changeover valve, reagent pump, and a reaction beaker via said changeover valve.

7 Claims, 11 Drawing Figures

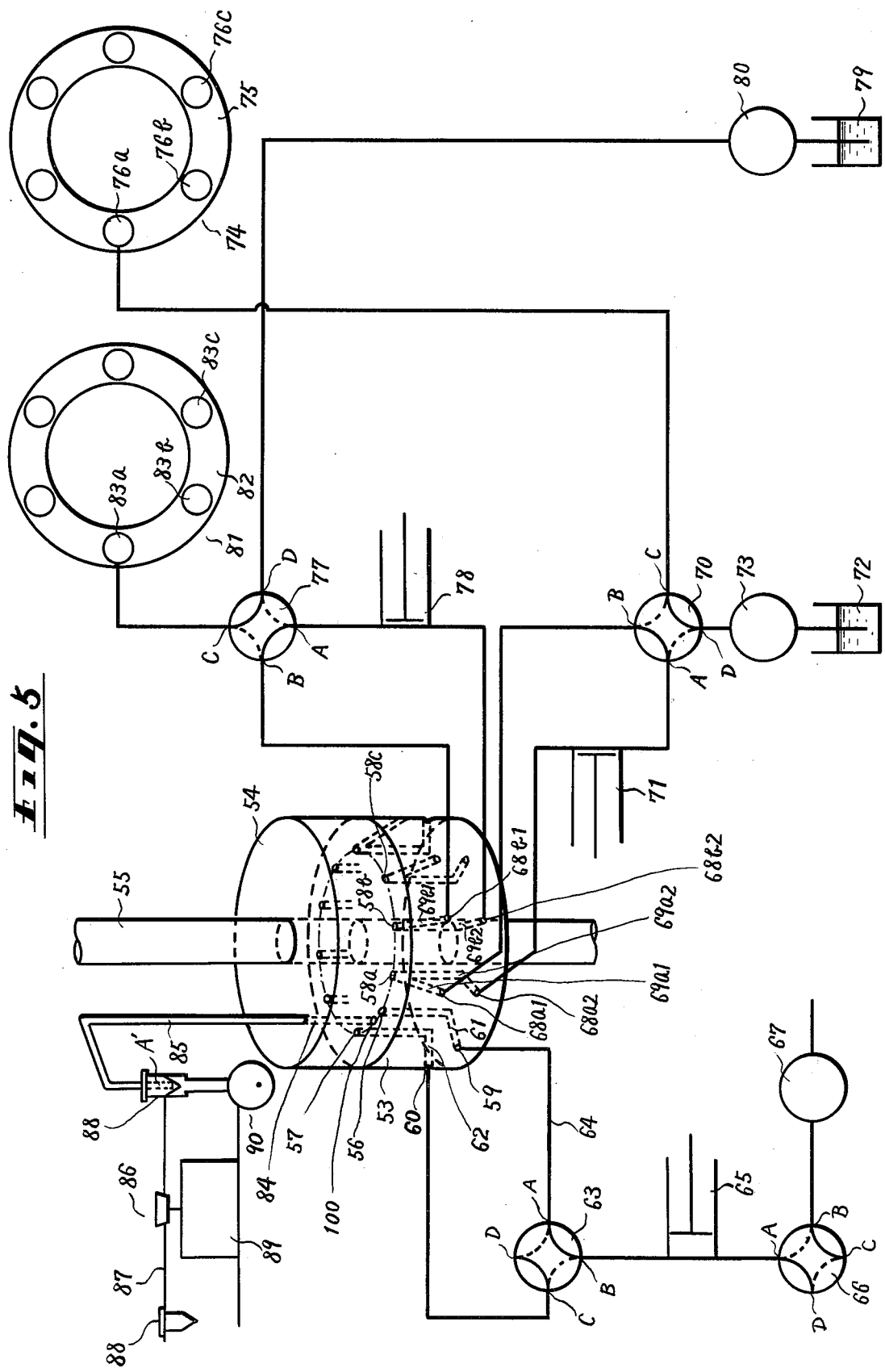

SAMPLING DEVICE

BACKGROUND

This invention relates to a sampling device for use in an automatic chemical analyzer.

Recently, in the field of chemical analysis, due to the large increase in the number of samples being treated, automatic analyzers have come to be widely used. In particular, there is a great demand for automatic analyzers capable of carrying out different kinds of analysis by repeatedly sampling small quantities of sample from the same container or receptacle. However, with this type of automatic analyzer, there is a need for a sampling device capable of measuring out small quantities of sample accurately and of preventing sample contamination due to repeated sampling.

Sample devices according to the prior art can be broadly classified into two types; the valve-cut type and the pipette type. The former type, as shown in FIG. 1, comprises a slide valve consisting of a sliding member 4, equipped with a sample measuring hole 3, sandwiched between two fixed bodies 1 and 2, said fixed bodies 1 and 2 being respectively provided with thru-ways 5 and 6, and 7 and 8 which are respectively connected to feed lines 9 and 10, 11 and 12, said feed lines being, in turn, connected to a sample suction pump 13, a reagent pump 15, a suction pipette 14, a discharge pipe 16 respectively. Operation of the valve-cut type sampler is as follows. First of all, the sliding member 4 moves so that the sample measuring hole 3 aligns with thru-ways 5 and 6. The sample suction pump 13 now commences to operate and a small quantity of sample is sucked up through pipette 14. As a result, thru-way 6 and measuring hole 3 fill up with liquid sample and thru-way 5 becomes partially filled with sample. Next, sliding member 4 moves so that the sample measuring hole 3 aligns with thru-ways 7 and 8. By so doing, the reagent pump 15 comes into operation and the sample, together with the reagent, passes through the discharge pipe 16 and into the reaction tube 18a. When the sample and reagent has entered the reaction tube 18a, the sliding member 4 returns to its original portion; i.e., measuring hole 3 once again aligns with thru-ways 5 and 6, and the suction pipette 14 moves over to a washing beaker 19. When this occurs, the action of the sample suction pump 13 is reversed so that the sample remaining in thru-ways 5 and 6, and feed lines 9 and 10, and any reagent remaining in measuring hole 3 is washed out. When this operation is complete, the pipette 14 moves either back to the sample tube 17a if repeated sampling of the same sample is intended or to another sample tube; e.g., sample tube 17b, if a different sample is to be sampled, and the same process as heretofore described, is repeated.

Although the above described valve-cut type sampling device possesses high reproducibility, it does have a disadvantage in that excess sample; i.e., the sample in thru-ways 5 and 6 which is not used for actual analysis, is sucked up in order to fill measuring hole 3 when the suction pump 13 is operated. And, since the amount of excess sample, as compared with the amount used for actual analysis, is large, sample utilization efficiency is poor which makes this type of sampling device unsuitable for measuring out and sampling minute quantities of sample. In addition to which, when the suction pipette 14 is reinserted into the sample tube after being washed, small drops of water adhering to the pipette are deposited into the liquid sample, thereby causing contamination. If there is only one sampling from each sample tube, this does not present much of a problem but in the case of repeated sampling from the same tube, the problem of contamination becomes consequential.

On the other hand, the latter type of sampling device (viz., the pipette type sampler) is shown in FIG. 2. In FIG. 2a, the sample suction pump 20 and the pipette 21 are connected directly. In this case, a fixed amount of sample is sucked up from the sample tube 22 through a pipette 21 by the action of the sample suction pump 20. The pipette 21 then moves over to the reaction tube 23 and deposits its contents therein. This completed, the pipette moves over to the washing beaker 24 and, after the pipette has been washed, the same process is repeated. In FIG. 2b, the pipette and suction pump are connected through a flow path changeover valve 25. In this case, one of the valve inlets is connected to a reagent pump 26 and a quantity of the sample is sucked up by the suction pump 20. After which, the valve operates so as to change over the sample flow path, the reagent pump then comes into operation and the sample is discharged into the reaction tube 23.

The pipette type of sampling device has an advantage in that structurally it is comparatively simple. However, the problem common to the valve-cut type of sampling device are present. For example, small drops of water remain on the tip of the pipette after washing which contaminate the unsampled sample in the case of repeated sampling. There is also the problem of sample cut-off at the pipette tip which makes precision sampling difficult, especially when dealing with very small quantities of sample.

In a nutshell, sampling devices according to the prior art, regardless of type, are incapable of completely preventing sample contamination if repeated sampling is carried out from the same sample tube or container. Thus, sample reproducibility deteriorates, a factor which becomes very pronounced when the sampling quantity is very small.

One object of the subject invention is to provide a sampling device capable of measuring out small quantities of sample accurately.

Another object of the subject invention is to provide a sampling device capable of measuring out sample under contamination-free conditions, regardless of sampling frequency.

Yet another object of the subject invention is to provide a sample measuring device having a high sample utilization efficiency.

Still another object of the subject invention is to provide a sample measuring device suitable for repeatedly and automatically measuring and sampling.

BRIEF SUMMARY OF THE INVENTION

According to this invention, a sampling device suitable for automatic chemical analysis comprises a rotating valve body and a fixed valve body, said rotating and fixed valve bodies having radial surfaces in sliding contact. The radial surface of the rotating body being provided with one or more internal sample outlet ports arranged on the circumference of a circle having its center coinciding with the axis of the rotating body. The side wall, for example, of said rotating body is provided with one or more external sample inlet ports. A duct joins each external sample inlet port with only one internal sample outlet port. The sample inlet ports in the side wall of said rotating body, for example, are each connected to a sample tube which rotates together with the rotating body. The radial surface of said fixed body in sliding contact with said rotating body is provided with a single internal inlet port located the same distance from the axis of the rotating body as the internal sample outlet ports. The internal sample inlet port is directly linked to two ports in the side wall of the fixed body by two ducts which join together at the internal inlet port. A first duct is connected to a changeover valve and a sample drawing pump. The other, or second, duct is connected to the changeover valve, also. The first duct may be connected to a reagent tank via the changeover valve and a reagent pump. The second duct may be connected to the reaction beaker via the valve. When an internal sample outlet port, concomitant with the stepwise rotation of said rotating body, becomes aligned with a single internal inlet port, a fixed quantity of sample may be drawn into the ducts of said fixed body upon activation of said sampling pump. At this time, the changeover valve isolates the ducts from the reagent tank and the reaction vessel. The rotating body is then rotated one step further so that no ports are aligned. The changeover valve is also rotated to put the ducts in communication with the reagent tank (via the reagent pump) and the reaction vessel. In this condition, the reagent pump comes into operation forcing reagent into said ducts via said valve which together with the sample flows into said reaction beaker via said valve. The configuration and operation mode as aforedescribed ensures accurate minute quantity samples as well as contamination-free sampling, regardless of sampling frequency.

BRIEF DESCRIPTION OF THE DRAWINGS

FIG. 5 shows another embodiment of the invention.

DETAILED DESCRIPTION OF THE INVENTION

Figure 1:
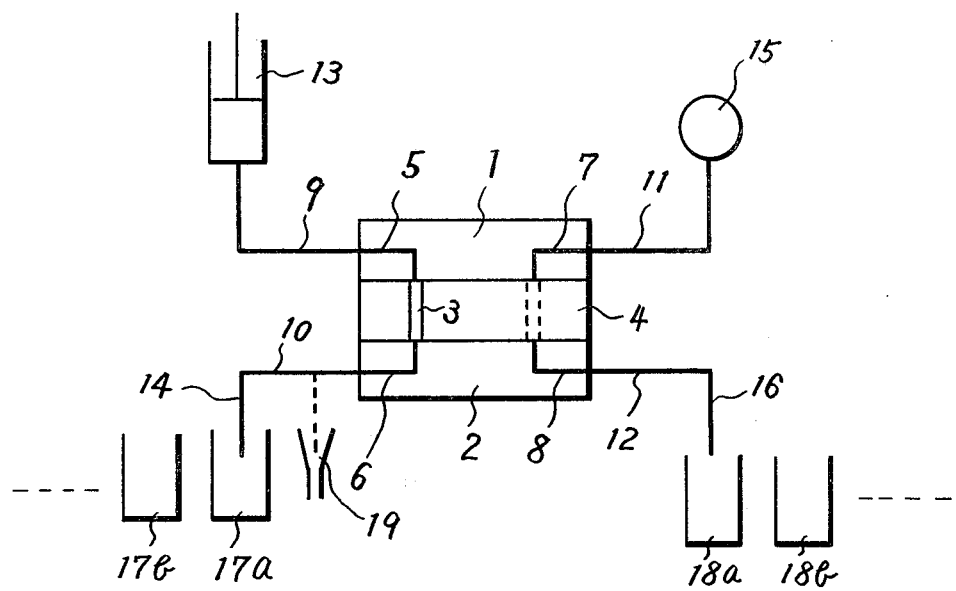
FIG. 1 shows one schematic drawing of the prior art.
Figure 2A:
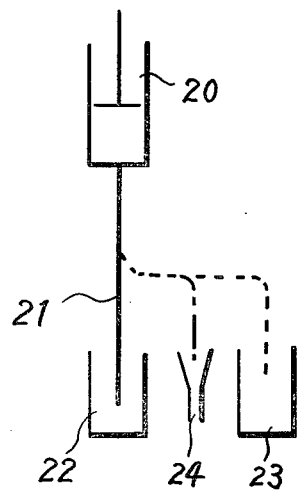
FIGS. 2(a) and (b) show schematic drawings of other prior art.
Figure 2B:
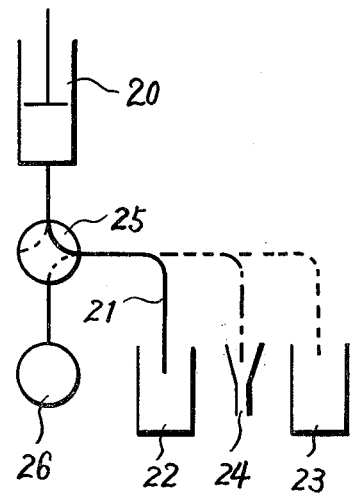
Figure 3:
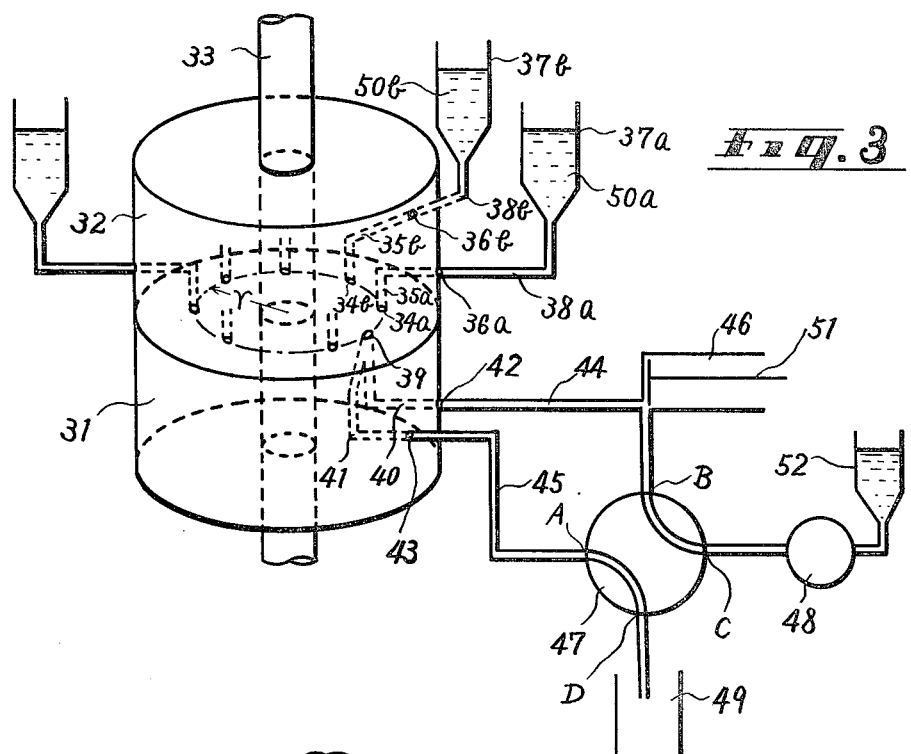
FIG. 3 shows one embodiment of the subject invention.

FIG. 3 shows one embodiment of the subject invention. In the figure, a fixed valve body 31 and a rotating valve body 32 are journaled on shaft 33 which guides the radial surface of rotating valve body 32 over the radial surface of the fixed valve body 31. The radial surface of the rotating valve body 32 in contact with the fixed valve body 31 is provided with a plurality of internal sample outlet portions 34a, 34b, etc. arranged equidistantly around a circle having a radius r with a center coincident with the axis of the shaft 33. The side wall of the rotating valve body 32 is provided with a plurality of external sample inlet ports 36a, 36b, etc. Ports 34a, 34b, etc. are linked to ports 36a, 36b, etc. respectively by ducts 35a, 35b, etc. A plurality of sample tubes 37a, 37b, etc. are connected to the external sample inlet ports 36a, 36b, etc. via feed lines 38a, 38b, etc. The radial surface of the fixed body 31 in sliding contact with the rotating valve body 32 is equipped with at least one internal sample inlet port 39 arranged the same distance from the axis of the shaft 33 as the other ports. Ports 42 and 43 are provided in the side wall (or base) of the fixed valve body 31, said ports 42 and 43 being directly linked to said internal sample inlet port 39 via ducts 40 and 41 respectively. Ducts 40 and 41 joined together at the sample inlet port 39. A sampling pump 46 is connected to port 42 via a feed line 44.

Port A of changeover 47 is connected to port 43 on the fixed body via a feed line 45. Ports B, C, D of said changeover valve 47 are connected to a sampling pump 46, a reagent tank 52 (via a reagent pump 48), and a reaction beaker 49 respectively.

In the embodiment as described above, the rotating body 32 initially rotates so as to establish a condition as shown in FIG. 3. That is to say, so that internal sample outlet ports 34a, 34b, etc. do not align with the internal sample inlet port 39. In this condition, samples 50a, 50b, etc. contained in sample tubes 37a, 37b, etc. flow out through feed lines 38a, 38b, etc. Next, the ducts 35a, 35b, etc. are filled with respective samples as follows: The rotating body 32 commences to turn stepwise so that internal sample outlet ports 34a, 34b, etc. register with internal sample inlet port 39 successively. As each outlet port (34a, etc.) registers with inlet port 39, the sampling pump 46 comes into operation and draws sample into ducts 40 and 41, said small amount of sample being allowed to drain into a waste bath (not shown) via feed line 45 and the flow path changeover valve 47.

Figure 4A:
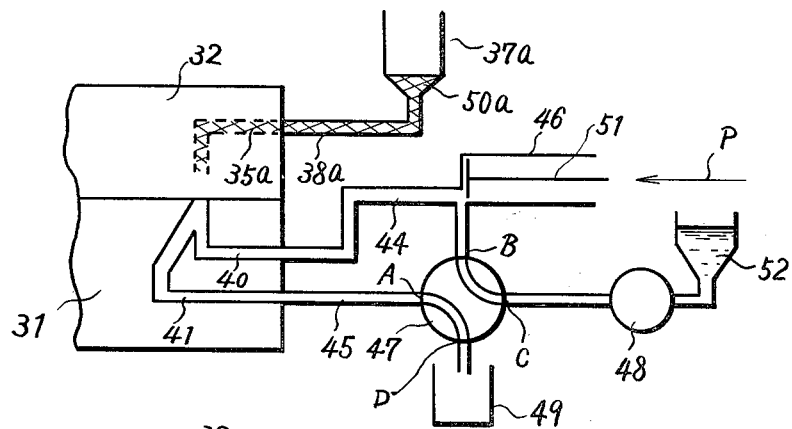
FIGS. 4(a), (b), (c), (d) and (e) are schematic drawings for explaining the operation of the embodiment according to FIG. 3.

Next, the changeover valve 47 operates so as to connect ports B to C and A to D, which is the reagent flush position, and the piston 51 of sampling pump 46 is moved towards the cylinder head. The reagent pump 48 now comes into operation with the result that feed line 44, ducts 40 and 41, and feed line 45 fill up with reagent from the reagent tank 52. This state of affairs is shown cross-sectionally in FIG. 4(a).

Figure 4B:
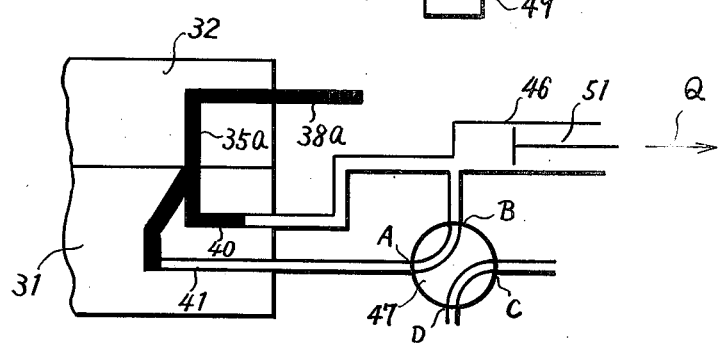

Sampling now commences. First of all, as illustrated in FIG. 4(b), the changeover valve 47 operates so as to connect ports A to B and C to D, which is the sample drawing position in which ducts 40 and 41 are not only connected at port 39 but through the changeover valve. The rotating body 32 rotates so that port 34a registers with port 39. (It is possible to place the changeover valve in an all ports closed position when drawing sample as explained hereafter. The advantage of externally connecting ducts 41 and 40 through the changeover valve during the sample drawing is that sample is drawn into both ducts 41 and 40. If the valve were placed in the all ports closed position, sample is drawn only into duct 40 and may reach the sample drawing piston which is not desired.)

Figure 4C:
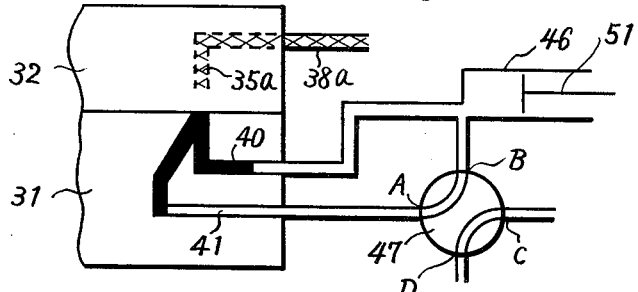

With the changeover valve now in the sample drawing position and the internal inlet port aligned with one internal outlet port, by withdrawing the piston 51 of sample drawing pump 46 in the direction indicated by the arrow Q a predetermined amount (thus enlarging the volume defined by the ducts 40, 41, 44, 45, the duct in the changeover valve and the sampling pump piston 51), a suitable volume of sample (corresponding to the increase in volume due to movement of the sampling pump piston) flows from duct 35a into ducts 40 and 41. The rotating body 32 then rotates so that the port 34a does not register with port 39 as shown in FIG. 4(c).

Figure 4D:
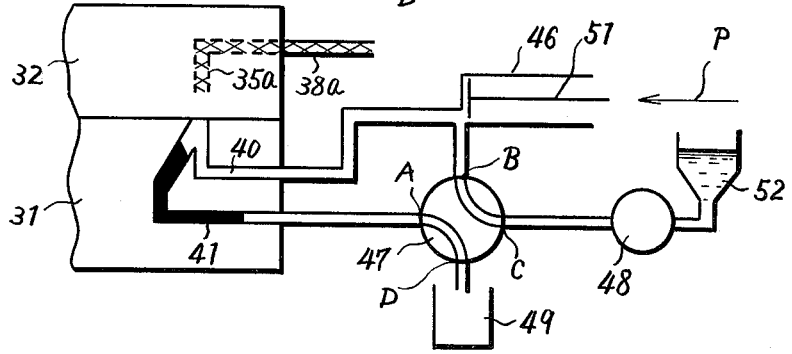
Figure 4E:
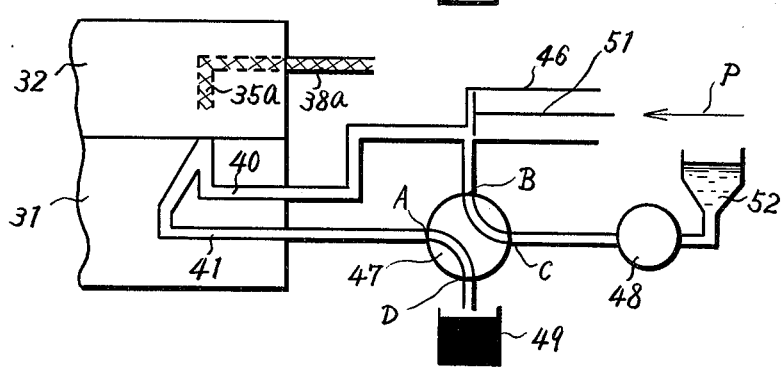

Next, the changeover valve 47 operates so as to revert to the B to C and A to D, position, i.e., the reagent flush position, as shown in FIG. 4(d). The piston 51 moves in the direction indicated by the arrow P. Additionaly, the reagent pump 48 is reactivated (FIG. 4(e)) and the reagent, together with the measured sample in ducts 40 and 41, is forced into the reaction beaker 49. Subsequently, sample from the same sample tube 37a or from another sample tube, e.g., sample tube 37b, is measured out and the same process as heretofore described is repeated.

In the above described embodiment, feed lines 38a, 38b, etc. run from the base of the respective sample tubes and link up with ports 36a, 36b, etc. As an alternative to this arrangement, sample tubes having a sealed base with feed lines inserted from above would be quite acceptable.

Further, by providing a plurality of internal sample inlet ports 39 instead of just a single port as described above, and by providing the requisite number of ducts (two per port), sampling of a plurality of samples can be carried out simultaneously. It is also possible to use two simple on-off changeover valves. In this case, one valve would be installed between pumps 46 and 48, and a second valve would serve to changeover feed line 45 and the reaction beaker 49. Both valves would be open connecting during the reagent flushing step and closed during the sample drawing steps.

In the subject invention as described in detail in the aforegoing, the exact amount of sample required for sampling is drawn into ducts 40 and 41 from duct 35 by the action of the sampling pump piston 51. The rotating body 32 then rotates to a position where ports 34 and 39 do not register; i.e., to a position where the sample in duct 35 is isolated from the measured sample in ducts 40 and 41. In this condition, the reagent pump then comes into operation and forces the measured sample together with a quantity of reagent, into reaction beaker 49.

Thus, with such a system, repeated sampling from the same sample source can be carried out without having to worry about sample contamination. Further, since only the amount of sample used for actual analysis is measured out, there is no sample wastage. In other words, a sampling device having a high sample utilization efficiency is provided. Lastly, the sample cut-off problem, peculiar to the pipette type sampling device, is eliminated.

FIG. 5 shows another embodiment of this invention in which fixed body 53 and a rotating body 54 are journaled together with shaft 55 which rotates said rotating body 54 having a radial surface sliding over a radial surface of the fixed body 53. The radial surface of the fixed body 53 is provided with washer port 57 and sample drawing port 56, and internal sample inlet ports 58a, 58b, 58c etc. arranged equidistantly around a circle having a radius r with its center coincident with the axis of shaft 55. Ports 56, 57 are linked to ports 59, 60 provided in the side wall of the fixed body 53, by ducts 61, 62 respectively. Port 59 is connected to port A of a changeover valve 63 via a feed line 64, and ports B, C of said changeover valve 63 are connected to port A of a second changeover valve 66 via a sampling pump 65, and to port 60, respectively. Port B of changeover valve 66 is connected to a washing pump 67. Port 58a is directly linked to a pair of ports 68a1, 68a2 via ducts 69a1, 69a2, respectively and port 58b is directly linked to a second pair of ports 68b1, 68b2 via ducts 69b1, 69b2, also respectively. The remaining ports 58c, 58d, etc. are similarly linked via ducts. Port 68a2 is connected to port A of a flow path changeover valve 70 via a sampling pump 71, and ports B, D of said flow path changeover valve 70 are connected to port 68a1 directly and a first reagent tank 72 via a reagent pump 73, respectively. Port C of said changeover valve 70 is connected to a first rotating reaction device 74 comprising a rotating member 75 which accommodates a plurality of reaction beakers 76a, 76b, 76c, etc. and a driving means (not shown) which intermittently rotates the rotating member 75. Similarly, port 68b2 is connected to port A of a changeover valve 77 via a sampling pump 78, and ports B, D of said flow path changeover valve 77 are connected to port 68b1 directly and a second reagent tank 79 via a reagent pump 80, respectively. Port C of said flow path changeover valve 77 is connected to a second rotating reaction device 81 comprising a rotating member 82 which accommodates a plurality of reaction beakers 83a, 83b, etc., and a driving means (not shown) which intermittently rotates the rotating member 82. The surface of the rotating body 54 in contact with the fixed body 53 is also equipped with an internal sample outlet port 100, said port 100 being linked via a duct 84 to a sample suction tube 85, the latter of which is fixed to said rotating body 54 and rotates together therewith. Now, when the rotating body 54 rotates so that the port 100 registers with port 56, the head A' of the sample suction tube 85 is positioned on a circle around which many sample tubes 88, supported by a sample supply device 86, are arranged. Further, when the rotating body 54 again rotates so that the port 100 registers with port 57, the head A' of the sample suction tube 85 is positioned over a waste bath (not shown). The sample supply device 86 comprises a turntable 87 equipped with peripheral holes for accommodating said plurality of sample tubes 88, a driving means 89 for rotating said turntable 87, and a cam-operated sample tube shifting device 90 for raising and lowering any sample tube positioned thereon, so as to insert head A' of the sample suction tube 85 into the sample tube, filled with sample, next in line for analysis.

In this embodiment described with reference to FIG. 5, the rotating body 54 is initially positioned so that internal sample outlet 100 registers with washing port 57. That is to say, so that the head A' of suction tube 85 is positioned over the aforementioned waste bath (not shown). Thus positioned, the changeover valve 63 operates so as to connect ports B to C and A to D, and the flow path changeover valve 66 operates so as to connect ports A to B and C to D. At the same time, the piston of sampling pump 65 is compressed (inwards) towards the cylinder head. The washing pump 67 then comes into operation and water is drawn up into duct 84, sample suction tube 85, and out through the suction tube head A' into the waste bath via flow path valve 66, sampling pump 65, changeover valve 63 and duct 62. After the cleaning operation is completed, the changeover valve 63 operates so as to connect ports A to B and C to D, and the changeover valve 66 operates so as to connect ports A to D and B to C. The rotating body 54 then rotates so that internal sample outlet port 100 aligns with sample drawing port 56, thus positioning the head A' of the sample suction tube 85 over one of the sample tubes 88. Next, the sample tube shifting device 90 operates so as to raise the sample tube in question, thereby inserting the head A' of said sample suction tube 85 therein. The sampling pump 65 now comes into operation and draws a certain amount of sample into the sample suction tube 85 and ducts 84 and 61. This completed, the changeover valve 70 operates so as to connect ports A, B and C, D, the sample tube shifting device 90 operates to lower the sample tube, the rotating body 54 rotates so that port 100 registers with port 58a and the sampling pump 71 comes into operation so as to draw a predetermined amount of sample into ducts 69a1 and 69a2.

Next, the changeover valve 77 operates so as to connect ports A, B and C, D, the rotating body 54 rotates to a position where port 100 aligns with port 58b, and the sampling pump 78 comes into operation so as to draw a predetermined amount of sample into duct 69b1 and 69b2. The above operational sequence is repeated until all the pairs of ducts, viz., 69c1, 69c2, 69d1, 69d2, etc., contain a fixed quantity of sample. The rotating body 54, then rotates to a position, where the thru-hole 100 does not register with any of the ports, the changeover valves 70, 77, etc. operate so as to connect ports A, D and B, C. Finally reagent pumps 73, 80, etc. come into operation in sequence so as to force the measured sample in the respective pairs of ducts (69a1, 69a2), (69b1, 69b2), etc., together with a quantity of reagent, into reaction beakers 76a, 83a, etc.

Figure 6:
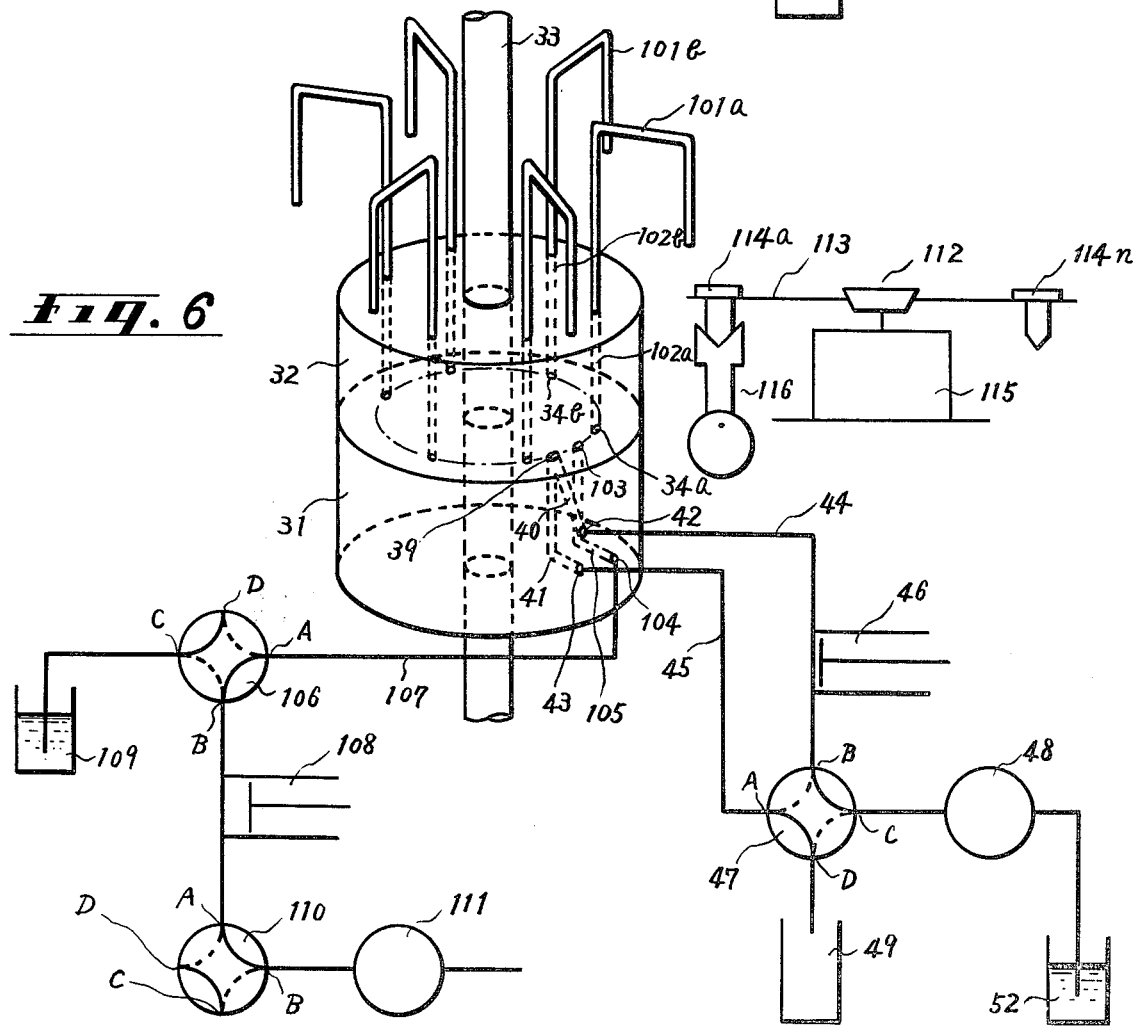
FIG. 6 shows yet another embodiment of the invention.

FIG. 6 shows yet another embodiment of this invention which lends itself more practically to automatic chemical analysis of the sample than the previously described embodiments. In the figure, the constituent parts having index numbers corresponding to those in FIG. 3 are identical. In this embodiment, however, the rotating body 32 is equipped with a plurality of sample suction tubes 101a, 101b, etc. instead of the bulkier sample tubes 37a, 37b, etc. as in the case of the embodiment according to FIG. 3. The rotating body 32 is also equipped with ducts 102a, 102b, etc. linking said sample suction tub3es 101a, 101b, etc. to internal sample inlet ports 34a, 34b, etc, respectively. Moreover, the surface of the fixed body 31 in contact with the rotating body 32 has been provided with an extra washing port 103 which is linked to port 104 via a duct 105. An additional circuit comprising two changeover valves 106, 110, a sampling pump 108, a waste bath 109, and a washing pump 111 has been included, port A of the flow path valve 106 being connected to port 104 via a feed line 107. In this embodiment, the sample is supplied by a sample supply device 112 which is composed of a turntable 113 for accommodating a plurality of sample tubes 114a, etc., a rotating means 115 for rotating the turntable 113 stepwise, and a sample tube shifting means 116 for raising and lowering the sample tubes 114a, etc.

The washing and sampling procedure is described as follows. First of all, the flow path valves 106 and 110 operate so as to connect ports A, B and C, D, respectively. The rotating body 32 then rotates and stops rotating when internal sample inlet port 34a aligns with washing port 103. Thus positioned, the washing pump 111 comes into operation and water flows through duct 105, duct 102a and sample suction tube 101a, spilling out into a waste bath (not shown). After thoroughly cleansing said sample suction tube 101a, the washing pump 111 stops and the rotating body 32 rotates a further step so as to register port 34b with the port 103. The washing pump 111 again comes into operation and the washing procedure is repeated this time cleansing sample suction tube 101b. The rotating body 32 continues its stepwise rotation and the washing procedure is further repeated until all the sample suction tubes are clean. Next, the changeover valve 110 operates so as to connect ports A, D and B, C, respectively and the rotating body 32 rotates so as to register ports 34a with ports 103. This completed, the turntable 113 rotates to position sample tube 114a underneath suction tube 101a, and the sample tube shifting device 116 operates to raise said sample tube 114a, thereby allowing the head of the sample suction tube to enter therein. The sampling pump 108 then operates so as to draw the piston away from the cylinder head and thereby suck a predetermined amount of sample into the sample suction tube 101a, the changeover valve 106 operates to connect ports A, D and B, C, respectively and the piston of the sampling pump 108 returns to its original position. Then, valve 106 again operates to connect ports A, B and C, D and finally the sample tube shifting means 116 operates to lower the sample tube 114a. The rotating body 32 now rotates one more step to register port 34b with washing port 103 and the above process is repeated. As a result, sample suction tube 101b is changed with a fixed amount of sample from the next sample tube 114b (now shown). The above process is further repeated until all the sample suction tubes contain sample from the respective sample tubes. This completed, changeover valve 47 operates to connect ports A, B and C, D, the rotating body 32 rotates so as to register port 34a with port 39, the sampling pump 46 operates to draw a predetermined amount of sample from the sample suction tube 101a into ducts 40 and 41, valve 47 again operates to connect ports A, D and B, C, the reagent pump 48 operates to draw a quantity of reagent from the reagent tank 52 into ducts 40 and 41 which, together with the sample already in said ducts 40 and 41, flows into the reaction tube 49. The same process is repeated until the sample in the remaining sample suction tubes has been mixed with reagent and deposited in the reaction tube 49. In this way, the sample in each sample suction tube is automatically analyzed in sequence.

Having thus described my invention in detail and with the particularity as required by the Patent Laws, what is desired protected by Letters Patent is set forth in the following claims.

I claim:

1. A sampling device comprising first and second valve bodies, said bodies having abutting faces in sliding contact and being movable relative one to the other, said first body having at least one sample holding duct which may be filled with sample, said sample holding duct opening through an internal sample outlet port in the abutting face of said first body, said second body having at least one pair of ducts each duct of said pair directly connected to an internal sample inlet port in the abutting face of the second body, means for bringing the ports into registration and moving them out of registration, at least one sampling pump connected to at least one duct in each said pair of ducts in the second body, said sampling pump arranged to draw the sample through internal outlet and internal inlet ports when they are in registration, said at least one pair of ducts in said second body connected such that the sample drawn may be discharged therefore when no ports are in registration.

2. A sampling device according to claim 1 in which said at least one sample holding duct of said first body is connected to a sample tube fixed to said first body.

3. A sampling device according to claim 1 in which said at least one sample holding duct of said first body is connected to a sample suction tube fixed to said first body.

4. A sampling device according to claim 1 in which said first body is rotated about an axis of rotation and said second body is fixed and whereby the said ports are all spaced an equal distance from the axis of rotation.

5. A sampling device comprising first and second bodies, said bodies having abutting faces in sliding contact and rotating about an axis relative one to the other, said first body having at least one sample holding duct connected to a sample suction tube and an internal sample outlet port positioned a preselected distance from said axis on the abutting face of said first body, said second body having at least one pair of sampling ducts each duct of the pair directly connected to an internal sample inlet port positioned said preselected distance from the axis of rotation, said sample inlet port opening through the abutting surface of said second body, said second body also having a drawing duct connected to a drawing port opening through the abutting surface of said second body being positioned said preselected distance from said axis, a drawing pump for drawing sample into said sample suction tube when an internal sample outlet port of said first body and said drawing duct are rotated to align, at least one sample pump connected to one of said at least one pair of sampling ducts in said second body, said sampling pump for drawing the sample from a sample holding duct through internal outlet and internal inlet ports when said ports are rotated to align, said pair of ducts in the second body connected such that the sample drawn through said internal inlet and outlet ports may be discharged from the ducts when all ports of said first and second bodies are rotated to not align.

6. A sampling device comprising first and second bodies, said bodies rotating about an axis relative to each other, said first body having at least one duct connected to a sample suction tube and an internal outlet port arranged on a circle having an optional diameter and its center at the axis of rotation, said port being on a surface of said first body in sliding contact with said second body said second body having at least one pair of sampling ducts each duct in a pair directly connected to an internal inlet port arranged on said circle, on the surface of said second body in sliding contact with said first body, said second body also having a drawing duct and a washing duct, said ducts being connected to ports on said circle, on the surface of said second body in sliding contact with said first body, a drawing pump for drawing sample into said sample suction tube when said ports of said first body and said drawing duct are aligned, a washing pump for washing said sample suction tube when said ports of said first body and said washing duct are aligned, at least one sampling pump connected to one of said at least one pair of sampling ducts, said sampling pump for drawing the sample into said pair of sampling ducts when internal outlet and inlet ports are aligned, said pair of ducts being connected such that the sample drawn into said pair of ducts may be discharged when all said ports of said first and second bodies are not aligned.

7. An automatic chemical analyzer comprising:
A) two bodies, a first body and a second body, said bodies rotated relatively about an axis, said first body having at least one duct connected to a sample suction tube and a port arranged on a circle having an optional diameter and a center coincident with the axis, said port opening on the surface of said first body in sliding contact with said second body, said second body having a plurality of pairs of sampling ducts, each of said pairs of sampling ducts being directly connected to one of a plurality of ports on the surface of said second body in sliding contact with said first body, said ports also opening onto said circle, said second body having a drawing duct and a washing duct connected to ports on the surface of said second body in contact with said first body, said ports also opening onto said circle;
B. a washing pump for washing said duct of said first body and said sample suction tube when said ports of said first body and said washing duct are in communication;
C. a drawing pump for drawing sample into said sample suction tube when said ports of said first body and said drawing ducts are in communication;
D. a plurality of sampling pumps, each sampling pump being connected to one duct of each said pairs of sampling ducts, said sample being drawn into any one of said pairs of sampling ducts when a port of the first body and said any one of said pairs of sampling ducts are in communication;
E. a plurality of reagent pumps for supplying reagent to said pairs of sampling ducts, and
F. a plurality of reaction vessels for receiving the sample drawn into said pairs of sampling ducts, and a quantity of reagent, said sample and reagent forced into said reaction vessels by said respective reagent pumps.

* * * * *

UNITED STATES PATENT AND TRADEMARK OFFICE
CERTIFICATE OF CORRECTION

PATENT NO. : 4,120,661
DATED : October 17, 1978
INVENTOR(S) : Toyohiko Naono

It is certified that error appears in the above-identified patent and that said Letters Patent are hereby corrected as shown below:

Column 1 Line 43 "portion" should read --position--.

Column 3 Line 56 "portions" should read --ports--.

Column 4 Line 7 After "changeover" insert --valve--.

Column 4 Line 49 "piston" should read --position--.

Column 7 Line 30 "tub3es" should read --tubes--.

Column 8 Line 13 "changed" should read --charged--.

Signed and Sealed this

Twenty-seventh Day of February 1979

[SEAL]

Attest:

RUTH C. MASON
Attesting Officer

DONALD W. BANNER
Commissioner of Patents and Trademarks